United States Patent [19]

Ichihara

[11] Patent Number: 4,692,624

[45] Date of Patent: Sep. 8, 1987

[54] EMISSION COMPUTED TOMOGRAPHY APPARATUS

[75] Inventor: Takashi Ichihara, Ootawara, Japan

[73] Assignee: Kabushiki Kaisha Toshiba, Kawasaki, Japan

[21] Appl. No.: 850,048

[22] Filed: Apr. 10, 1986

[30] Foreign Application Priority Data

Apr. 11, 1985 [JP] Japan ................................. 60-78029

[51] Int. Cl.$^4$ ........................................... G01T 1/164
[52] U.S. Cl. ................................. 250/363 S; 250/369
[58] Field of Search .................. 250/363 SB, 363 SC, 250/369, 363 SE; 364/414

[56] References Cited

U.S. PATENT DOCUMENTS 3,970,853  7/1976  Kuhl et al. ..................... 250/363 SB
4,434,369  2/1984  Metal ................................... 250/369

FOREIGN PATENT DOCUMENTS 0092437  10/1983  European Pat. Off. .
53673    3/1982   Japan ............................. 250/363 SB

OTHER PUBLICATIONS

Gottschalk et al., "SPECT Resolution and Uniformity Improvements by Noncircular Orbit," Journal of Nuclear Medicine, vol. 24, No. 9, pp. 822–828, Sep. 1983.
Patent Abstracts of Japan, vol. 7, No. 32 (P-174) [1177], Feb. 8, 1983; & JP-A-57 184 988 (Tokyo Shibaura Denki K.K.) Nov. 13, 1982.

*Primary Examiner*—Carolyn E. Fields
*Attorney, Agent, or Firm*—Finnegan, Henderson, Farabow, Garrett & Dunner

[57] ABSTRACT

An emission computed tomography apparatus in which a radiation detector is moved along an elliptical orbit about a subject under examination. The effective field of view of the radiation detector is reduced depending on the position of the detector. The reduction of the field of view produces a false image in a reconstructed image and reduces spatial resolution. To prevent this, part of image data, collected by the detector at a first position, for part of the subject from which radiation cannot be detected due to the reduced effective field of view, is interpolated with part of image data, collected by the detector at a second position, for the part of the subject from which radiation cannot be detected at the first position. The first and second positions are opposite to each other with the subject interposed therebetween.

2 Claims, 5 Drawing Figures

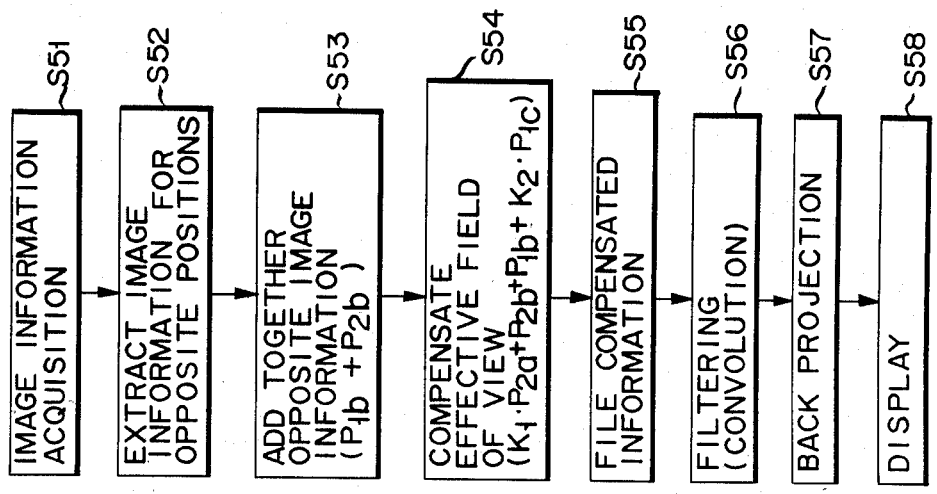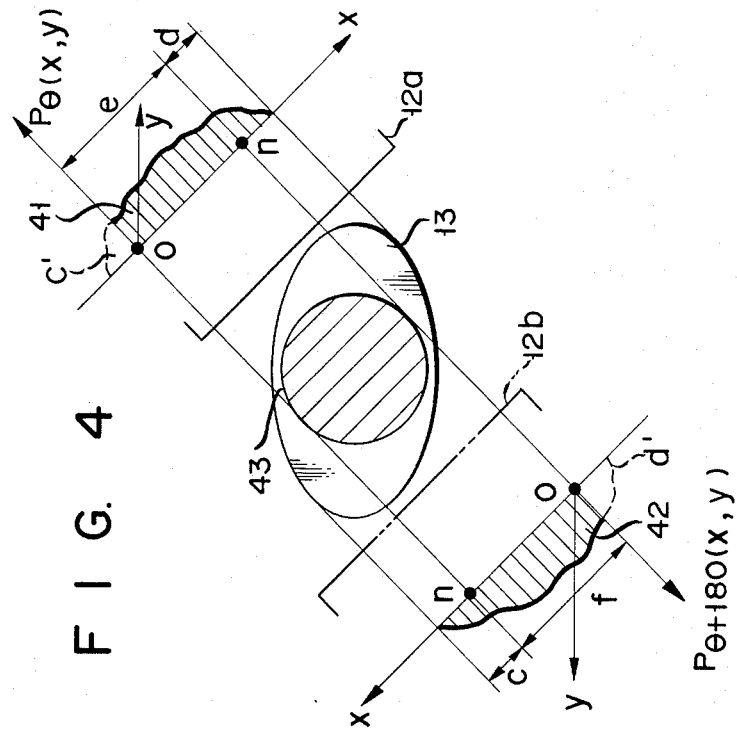

EMISSION COMPUTED TOMOGRAPHY APPARATUS

BACKGROUND OF THE INVENTION

This invention relates to an emission computed tomography apparatus for obtaining a scintigram of a subject dosed with radioisotope (RI).

Prior art emission computed tomography apparatuses use an Anger type gamma camera for detecting gamma rays emitted from the interior of a subject (human patient) under examination. The gamma camera head is rotated stepwise or continuous about the subject to collect gamma rays emitted therefrom in 360-degree directions. The gamma ray detection data is processed to reconstruct a tomogram image representing an RI distribution of the subject.

The gamma camera head has a parallel-hole collimator mounted on the front side thereof. Because of the property of the collimator, the resolution of detection is reduced with an increase in the distance between the collimator and subject. With the prior art emission computed tomography apparatus, therefore, the gamma camera head is moved along an elliptical orbit centered at a body axis of the subject, in order to move the camera head as close to the subject as possible so as to improve the detection resolution.

However, when the gamma camera head is moved along an elliptical orbit, a line passing through the center of the effective field of vision of the camera does not always pass through the body axis (center of revolution) of the subject. For this reason, (360-degree direction) projection data cannot be gained for a portion of the subject. Therefore, with the prior art emission computed tomography apparatus, a false image (which is called artifact in this field) is liable to appear in a reconstructed tomographic image of the subject, and spatial resolution is reduced. Therefore, it is difficult to obtain data suitable for diagnosis.

SUMMARY OF THE INVENTION

An object of the invention is to provide an emission computed tomography apparatus, which has a gamma camera head driven along an elliptical orbit and is arranged to obtain a tomogram of a subject suitable for diagnosis thereof.

The emission computed tomography apparatus according to the invention comprises a radiation detector for detecting radiation information from a subject dosed with radioisotope while moving along an elliptical orbit about the subject, the radiation detector having a predetermined effective field of view to detect perpendicular incident radiation, and a region of the subject from which radiation can be detected in 360-degree directions is restricted due to the elliptical orbit of the radiation detector so that the effective field of view is reduced, an image reconstruction section for reconstructing a tomogram representing a radiation distribution of the subject, and a display section for displaying an image reconstructed by the image reconstruction section.

To attain the above object of the invention, the image reconstruction section is arranged to interpolate a first part of image data collected by the radiation detector at a first position, the first part of image data corresponding a position of the subject that cannot be detected by the detector due to the reduced effective field of view of the detector, with a second part of image data collected by the detector at a second position opposite to the first position with the subject interposed therebetween, the second part of image data corresponding to data for the portion of the subject that cannot be detected by the detector at the first position.

BRIEF DESCRIPTION OF THE DRAWINGS

FIG. 4 is a diagram for explaining the operation of the enlarging compensation of effective field of view according to the invention; and FIG. 5 is a flow chart for explaining the operation according to the invention.

DETAILED DESCRIPTION OF THE PREFERRED EMBODIMENTS

Figure 1:
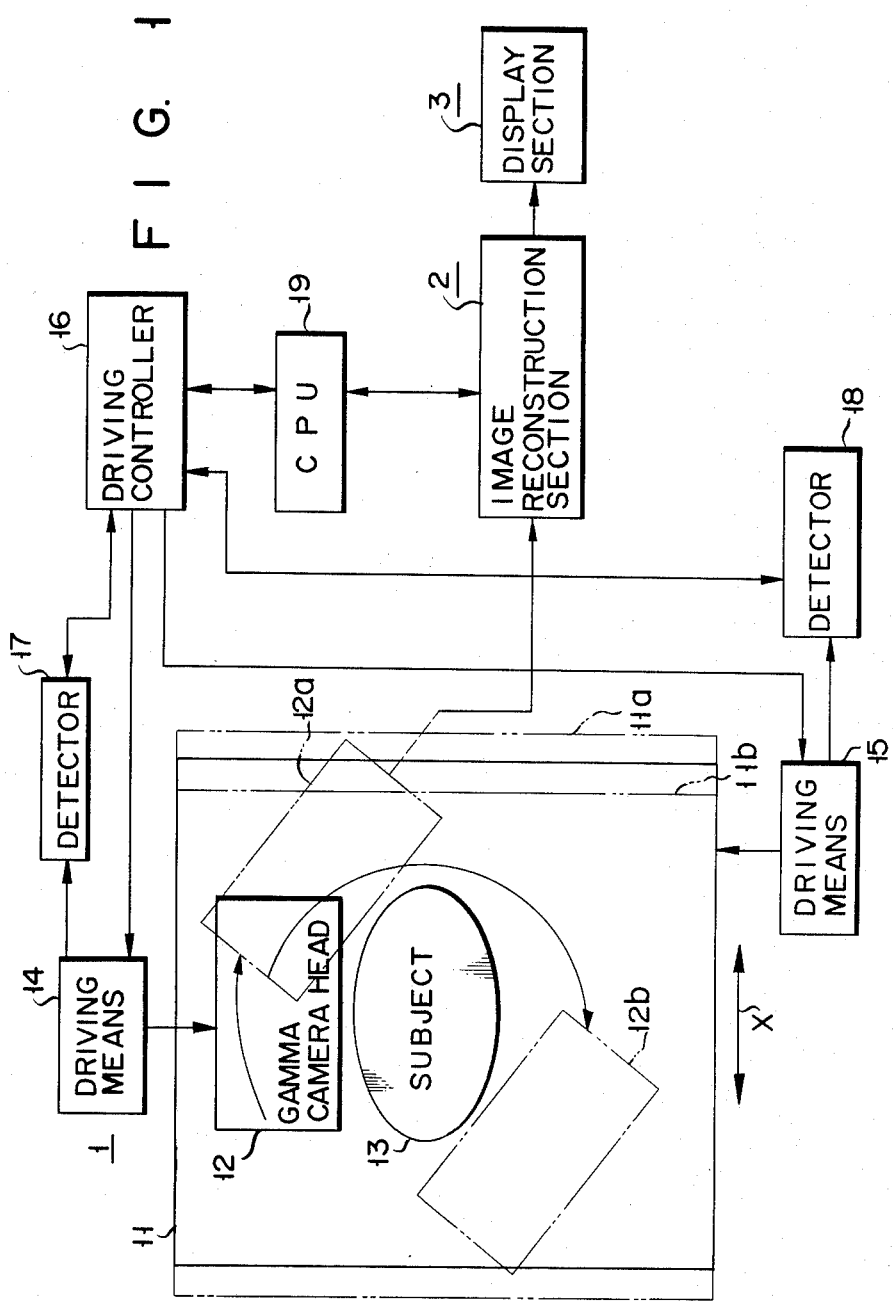
FIG. 1 shows a schematic arrangement of an emission computed tomography apparatus according to the invention.

Referring to FIG. 1, an emission computed tomography apparatus according to the invention comprises a detection section 1, image reconstruction section (data processing section) 2 and display section 3. Detection section 1 has a gantry 11 which supports a detector (gamma camera head) 12 so as to be capable of being rotated about a subject 13 lying on a couch (not shown) as shown at 12a and 12b, and can be moved in directions of arrows X, as shown at 11a and 11b. To this end, detector driving means 14 is provided for rotating detector 11 about subject 13 and gantry driving means 15 for moving gantry 11 in the directions of arrows X. Both driving means 14 and 15 are controlled by driving controller 16. The rotational angle of detector 12 is detected by detector 17, and the length of movement of gantry 11 is detected by detector 18. Detectors 17 and 18 are coupled to driving controller 16.

Detector 12 detects gamma rays emitted from subject 13 while rotating thereabout either continuously or stepwise at an angle of 10 degrees, for instance. Output data of detector 12 (which is X, Y position signals) is fed to image reconstruction section 2 to produce tomogram information signals representing RI distribution of the subject. The tomogram information signals are fed to display section 3 for visually displaying a tomogram of the subject. Driving controller 16 and image reconstruction section 2 are coupled to central processing unit (CPU) 19, to control gantry 11 and detector 12 and perform image processing in image reconstruction section 2.

Figure 2:
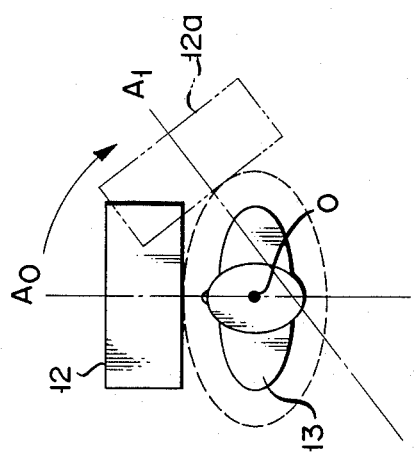
FIG. 2 is a diagram for explaining reduction of the effective field of view of a radiation detector which is driven along an elliptical orbit.

In practice, detector 12 is driven along a circular orbit by driving means 14. Since gantry 11 is moved in the directions of arrows X, detector 12 is effectively moved along an elliptical orbit about the subject, as shown in FIG. 2. As seen in FIG. 2, when detector 12 is positioned in front of subject 13, a line A0 passing through the center of the effective field of view of detector 12 passes through the body axis 0 of subject 13. However, when the detector is moved as shown at 12a, the center line A1 of the effective field of view no longer passes through the body axis 0 of subject 13. A portion of the subject under examination thus goes out of the effective field of view of the detector. This means that the portion of the subject cannot be detected. The invention intends to compensate the reduction in the effective field of view of the detector.

Figure 3:
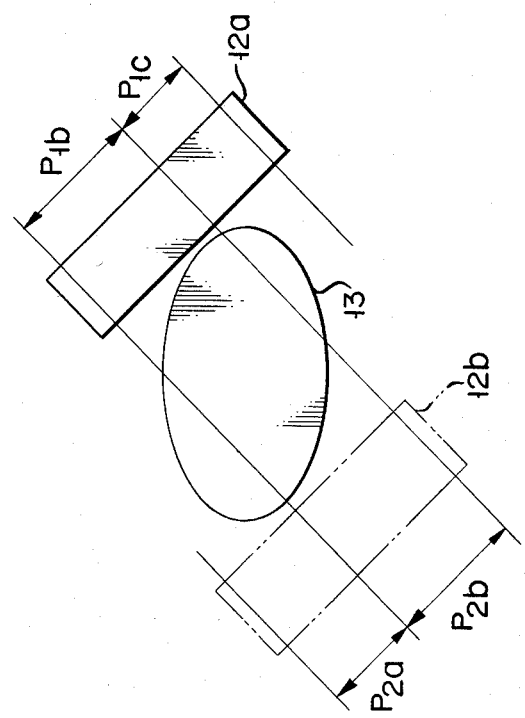
FIG. 3 is a diagram for explaining enlarging compensation of the effective field of view of the detector.

The reduction of the effective field of view of the detector will be described in more detail with reference to FIG. 3.

When detector 12 is at opposed positions 12a and 12b as shown, the effective field of view of the detector is represented by P1b+P1c (=P2a+P2b). The detector can detect gamma rays which perpendicularly fall on the detector within the effective field of view. Since the detector moves along an elliptical orbit about the subject, a region where 360-degree direction data of subject 13 can be collected is restricted to Pb (=P1b=P2b). For this reason, the effective field of view of the detector is substantially reduced. Such a reduction of the effective field of view leads to generation of an artifact and deterioration of spatial resolution.

The enlarging compensation of the effective field of view of detector will now be described with reference to FIG. 4. The Figure shows profiles 41 and 42 of projection data collected by the detector at the corresponding positions shown in FIG. 3. The region where 360-degree direction data of the subject can be collected is only a region enclosed in circle 43 from the ground discussed above. Therefore, data profile 41 lacks data represented by c', while data profile 42 lacks data represented by d'. In the enlarging compensation of the effective field of view according to the invention, lacking data c' of data profile 41 is approximately interpolated with data c of data profile 42 collected at the opposed position. Also, lacking data d' of data profile 42 is approximately interpolated with data d of data profile 41. Thus, from a point of view of data subjected to filtering and back projection, the effective field of view of the detector can be regarded to be enlarged, so that a substantially perfect reconstructed image may be obtained.

The operation according to the invention will now be described with reference to the flow chart shown in FIG. 5.

In step S51 image data is collected. This is performed while detector 12 is either continuous or stepwise rotated, and moving gantry 11 in the directions of arrows X. Collected image data (i.e., slice data) at each position of the detector is stored in a magnetic disk file in image reconstruction section 2. Image data collected at opposed positions of the detector can be discriminated in the magnetic disk file. In step S52, data collected at opposite positions of the detector are extracted from the magnetic disk file. It is to be noted that the size of the region where 360-degree direction data can be collected, i.e., region 43 in FIG. 4, is known in advance. In other words, data region corresponding to region 43 in the slice data is known in advance. In step S53, image data P1b and P2b corresponding to region 43 are extracted from the opposite data and added together in CPU 19. In subsequent step S54, the effective field of view is compensated in CPU 19. In the compensation of the effective field of view, CPU 19 performs an arithmetic operation given by $$K1 \cdot P2a + (P2b + P1b) + K2 \cdot P1c \qquad (1)$$

where K1 and K2 are coefficients which are introduced smoothly join image areas corresponding to P2a and P1c to an image area corresponding to (P2b+P1b). A method of obtaining coefficients K1 and K2 will now be explained. In FIG. 4, data profile 41 obtained from the detector at rotational angle $\theta$ is denoted by $P\theta(x,y)$, and data profile obtained from the detector at rotational angle $(\theta+180°)$ is denoted by $P\theta+180°(x,y)$. Origin 0 of the coordinate system is held at one end of the effective field of view of the detector. To interpolate lacking data d' of data profile 42 with data d of data profile 41, the coefficient K1 is obtained from a relation $$P\theta(0,y) = K1 \cdot P\theta + 180°(n,y) \qquad (2)$$

To interpolate lacking data c' of data profile 41 with data c of data profile 42, coefficient K2 is obtained from a relation $$P\theta + 180°(0,y) = K2 \cdot P\theta(n,y) \qquad (3)$$

In equations (2) and (3), x=n corresponds to the diameter of region 43.

Image data obtained after the compensation of the effective field of view is filed in the magnetic disk file (step S55). The image data stored in the magnetic disk file is subjected to filtering (i.e., convolution) (step S56). In subsequent step S57, the image data is back projected to obtain the reconstructed image data (i.e., a tomogram representing the RI distribution). The reconstructed image is displayed on display section 3 (step S58).

What is claimed is:

1. An emission computed tomography apparatus comprising:

a radiation detector for detecting radiation from a subject dosed with radioisotope while moving along an elliptical orbit about said subject, said radiation detector having a predetermined effective field of view to detect perpendicularly incident radiation, said predetermined effective field of view being reduced because a region where radiation emitted from said subject in 360-degree directions can be detected is restricted due to said elliptical orbit of said radiation detector;

an image reconstruction section responsive to said radiation detector for reconstructing a tomogram representing a radiation distribution of said subject; and a display section for displaying an image reconstructed by said image reconstruction section;

said image reconstruction section being arranged to interpolate a first part of image data collected by said radiation detector at a first position, the first part of image data corresponding to a portion of the subject that cannot be detected by said detector due to the reduced effective field of view of said radiation detector, with a second part of image data collected by said radiation detector at a second position opposite to the first position with the subject interposed therebetween, the second part of image data corresponding to data for the portion of the subject that cannot be detected by said radiation detector at the first position.

2. An emission computed tomography apparatus comprising:

a radiation detector for detecting radiation from a subject dosed with radioisotope while moving along an elliptical orbit about said subject, said radiation detector having a predetermined effective field of view to detect perpendicularly incident radiation, said predetermined effective field of view being reduced because a region where radiation emitted from said subject in 360-degree directions can be detected is restricted due to said elliptical orbit of said radiation detector;

an image reconstruction section responsive to said radiation detector for reconstructing a tomogram representing radiation distribution in said subject; and a display unit for displaying an image reconstructed by said image reconstruction section;

said radiation detector having a first effective field-of-view region and a second effective field-of-view region at each of first and second positions opposed to each other with the subject interposed therebetween, said first effective field-of-view region at each of said first and second positions detecting radiation emitted from the same part of said subject, said second effective field of view of said detector at said first position detecting radiation emitted from part of said subject outside the effective field of view of said radiation detector at said second position, and said second effective field-of-view region at said second position detecting radiation emitted from part of said subject outside the effective field of view of said radiation detector at said first position;

said image reconstruction section being arranged to perform an arithmetic operation given by $$K1 \cdot P2a + (P2b + P1b) + K2 \cdot P1c$$

where P1b represents radiation information detected by said first effective field-of-view region of said radiation detector at said first position, P1c represents radiation information detected by said second effective field-of-view region of said radiation detector at said first position, P2b represents radiation information detected by said first effective field-of-view region of said radiation detector at said second position, P2a represents radiation information detected by said second effective field-of-view region of said radiation detector at said second position, and K1 and K2 represent coefficients.

* * * * *